US010823680B2

(12) United States Patent
Blank et al.

(10) Patent No.: US 10,823,680 B2
(45) Date of Patent: Nov. 3, 2020

(54) DEVICE FOR IDENTIFYING A DIAMOND (71) Applicants: Public Joint Stock Company "Alrosa", Respublika Sakha (Yakutia) (RU); Federal State Budgetary Institution "Technological Institute for Superhard and Novel Carbon Materials" FSBI TISNCM, Moscow (RU)

(72) Inventors: Vladimir Davydovich Blank, Moscow (RU); Andrei Vladimirovich Butenko, Moscow (RU); Victor Nikolaevich Denisov, Moscow (RU); Igor Victorovich Makarsky, Respublika Sakha (RU); Gennady Markovich Nikitin, Respublika Sakha (RU); Dmitry Nikolaevich Nikitin, Respublika Sakha (RU); Larisa Gennadievna Tarasova, Respublika Sakha (RU); Sergei Alexandrovich Terentiev, Moscow (RU); Sergei Yurievich Troschiev, Moscow (RU); Sergei Vyacheslavovich Udarov, Moscow (RU); Alexander Sergeevich Chaadaev, Respublika Sakha (RU)

(73) Assignees: Public Joint Stock Company "Alrosa", Respublika Sakba (RU); Federal State Budgetary Institution "Technological Institute for Superhard and Novel Carbon Materials" FSBI TISNCM, Moscow (RU)

( * ) Notice: Subject to any disclaimer, the term of this patent is extended or adjusted under 35 U.S.C. 154(b) by 0 days.

(21) Appl. No.: 16/328,083

(22) PCT Filed: Aug. 26, 2016

(86) PCT No.: PCT/RU2016/000576
§ 371 (c)(1),
(2) Date: Feb. 25, 2019

(87) PCT Pub. No.: WO2018/038628
PCT Pub. Date: Mar. 1, 2018

(65) Prior Publication Data
US 2019/0219513 A1  Jul. 18, 2019

(51) Int. Cl.
*G01N 21/87* (2006.01)
*G01N 21/64* (2006.01)
(Continued)

(52) U.S. Cl.
CPC .............. *G01N 21/87* (2013.01); *G01J 3/0254* (2013.01); *G01N 21/63* (2013.01); *G01N 21/64* (2013.01);
(Continued)

(58) Field of Classification Search
CPC ........ G01N 21/87; G01N 21/63; G01J 3/0254
See application file for complete search history.

(56) References Cited

U.S. PATENT DOCUMENTS

| 5,377,004 A | 12/1994 | Owen et al. |
| 5,386,295 A | 1/1995 | Switzlski et al. |

(Continued)

FOREIGN PATENT DOCUMENTS

| CH | 700695 A2 | 9/2010 |
| GB | 2516297 | 1/2015 |

(Continued)

OTHER PUBLICATIONS

International Search Report, dated May 18, 2017, for International Application No. PCT/RU2016/000576.
(Continued)

*Primary Examiner* — Hugh Maupin (74) *Attorney, Agent, or Firm* — Faegre Drinker Biddle & Reath LLP (57) ABSTRACT

A diamond identification apparatus relates to the field of examining natural and synthetic diamonds. The claimed apparatus for identifying a cut diamond comprises a measurement location with a measuring aperture at which the cut diamond to be examined is fixedly positioned; a movable optical system including a spectrometer, two sources of radiation at wavelengths of 250-280 nm and 350-380 nm, respectively, said two sources of radiation and the spectrometer being connected to the measurement location by optical fibres for inputting radiation into the cut diamond and by an optical fibre for outputting radiation from the cut diamond; and also a source of laser radiation at a wavelength of 532 nm and a microcontroller, wherein the cut diamond is positioned at the measurement location in such a way that the table of the diamond faces the measuring aperture of the measurement location, and the culet of the diamond is situated directly above the measuring aperture to which the optical fibres for inputting radiation and the optical fibre for outputting radiation are connected, and wherein the microcontroller is configured to control the alternate operation of the sources of radiation in a set time sequence, the movement of the optical system to allow the input of radiation into the cut diamond, and the processing of the spectrometer data.

11 Claims, 5 Drawing Sheets

(51) Int. Cl.
*G01J 3/02* (2006.01)
*G01N 21/63* (2006.01)
*G02B 27/09* (2006.01)
*G02B 27/30* (2006.01)

(52) U.S. Cl.
CPC ......... *G02B 27/0955* (2013.01); *G02B 27/30* (2013.01)

(56) References Cited

U.S. PATENT DOCUMENTS

| | | | |
|---|---|---|---|
| 5,883,389 A | 3/1999 | Spear et al. | |
| 8,878,145 B1 * | 11/2014 | Liu | G01N 21/87 250/461.1 |
| 2011/0292376 A1 | 12/2011 | Kukushkin et al. | |
| 2016/0178530 A1 * | 6/2016 | Davies | G01N 21/87 209/578 |
| 2017/0010217 A1 * | 1/2017 | Paleari | G01N 21/87 |

FOREIGN PATENT DOCUMENTS

| | | |
|---|---|---|
| GB | 2516297 A | 1/2015 |
| RU | 2267774 C2 | 1/2006 |
| RU | 3473607 | 10/2009 |
| WO | 8607457 A1 | 12/1986 |
| WO | 0206797 A1 | 1/2002 |

OTHER PUBLICATIONS

Extended European Search Report dated Jul. 11, 2019 in European Application No. EP16914319, 10 pages.
B. Wang et al., "Study of probe-sample distance for biomedical for biomedical spectra measurement", Biomedical Engineering Online, Bio Med Central Ltd, London, GB, vol. 10., No. 1, p. 95, Feb. 11, 2011.

\* cited by examiner

DEVICE FOR IDENTIFYING A DIAMOND

CROSS REFERENCE TO RELATED APPLICATIONS

This application is a U.S. National Stage Application of International Patent Application No. PCT/RU2016/000576, filed Aug. 26, 2016, which is expressly incorporated by reference herein in its entirety.

TECHNICAL FIELD OF THE INVENTION

The present invention relates to the field of examining natural and synthetic diamonds and can be used for identifying and distinguishing natural diamonds from diamond simulants, and for separating natural diamonds from synthetic diamonds or from natural diamonds that have been subjected to a pressure-and-temperature treatment to improve color.

The importance of providing an apparatus for identifying diamonds, including brilliant-cut diamonds, is caused by increased frequency of market appearance of brilliants made of synthetic (HPHT and CVD) gem-quality diamonds and also made of diamonds subjected to a pressure-and-temperature treatment to improve color characteristics.

BACKGROUND OF THE INVENTION

A method and apparatus for examining gemstones are known (patent RU 2267774, publ. 10 Jan. 2006, IPC G01N21/87), the apparatus comprises a thermally-insulated container for containing the gemstone and having a window, means for cooling the container using liquid nitrogen, a cover for the container, a laser for irradiating said gemstone through the window, a spectrometer for detecting through said window photoluminescence spectra emitted by the gemstone and giving corresponding spectral data signals at its output, a blocking filter between said window and the spectrometer for filtering out radiation at the wavelength of the irradiating radiation, a processor connected to the output of the spectrometer, a display connected to the processor for displaying information regarding the gemstone, and a support structure, wherein said gemstone is directly immersed in the liquid nitrogen, the window is made in the container bottom near which a facet of the gemstone is placed, and said support structure mounts the foregoing components and provides a self-contained instrument, and wherein said laser and the spectrometer are coupled to said window. The apparatus can determine whether a polished gemstone is a natural diamond which has not been subjected to irradiation treatment and has not been subjected to high-pressure high-temperature treatment.

Disadvantages of the apparatus are an insufficiently high accuracy in identification of synthetic analogues of diamond (brilliant) and an inability of diagnostics of cut diamonds in jewelry.

An apparatus for sorting diamonds is known (patent RU 2372607, IPC G01N21/87, publ. 10 Nov. 2009), said apparatus using ultraviolet radiation for testing and distinguishing natural diamonds related to Types IIa, IIb and Ib. The sorting apparatus comprises an ultraviolet radiation source, a diamond crystal being tested, a radiation detector, a conversion amplifier, and a means for displaying the intensity of radiation transmitted through the diamond crystal. As the ultraviolet radiation source, the apparatus comprises an ultraviolet light-emitting diode (LED) with a radiation peak within the wavelength range of 240 to 300 nm and, as the radiation detector, comprises a photodiode with increased spectral sensitivity in shortwave ultraviolet region, wherein the ultraviolet LED is arranged in a holder with a table having a central aperture made therein for transmitting a directed radiation from the LED to the diamond crystal being tested which is placed on the table. An electrical signal from the photodiode is supplied to the conversion amplifier and further to the displaying means which registers a threshold intensity level of the radiation passing through the diamond crystal. The photodiode is placed in the holder so as to be able to change its position above the cut diamond crystal and to detect refracted radiation beams. To test round-shaped diamond crystals, the photodiode placed in the holder is fixed in a removable cover. The conversion amplifier is provided with a parallel output to connect a continuous digital signal indication meter during tuning and calibrating the apparatus.

This apparatus is incapable of determining whether the examined stone is a diamond or its simulant, and of distinguishing natural diamonds from synthetic ones.

An apparatus is known (U.S. Pat. No. 5,883,389, publ. 16 Mar. 1999, IPC G01N21/87), which allows for examining and distinguishing a natural diamond from synthetic diamonds by irradiating a diamond surface with ultraviolet radiation at a wavelength of 225 nm and for observing luminescence and/or phosphorescence. A device for irradiating a diamond with ultraviolet radiation is connected to a power supply and is focused by ultraviolet quartz lenses between which a filter is positioned, and a shutter is interposed in the light path after the lenses to quickly terminate the irradiation. A cut diamond (brilliant) is mounted in a holder having a handle for manipulation of the diamond. A mirror and a filter transmitting radiation with wavelengths in the range of 225-380 nm are positioned to direct light onto the diamond crystal.

A disadvantage of this apparatus is its restricted applicability in classification of diamonds.

A technical solution closest to the present invention is an apparatus described in the patent entitled "Measuring parameters of a cut gemstone" (patent GB 2516297, IPC G01N 21/87, publ. 1 Jan. 2015). The patent describes an apparatus comprising multiple light sources having different wavelengths directed through fibre optic inputs onto a cut diamond (gemstone) which is placed on a special measurement location. One of the sources emits in a broadband spectrum range of a 300 nm to 520 nm wavelength and allows for measuring absorption in the sample being examined, and also measures photoluminescence and phosphorescence. Incident excitation radiation is reflected from the cut diamond being examined and is fed through a fibre optic output to a spectrometer and is subjected to analysis therein. The spectrometer is in turn connected to a processor (a computer and/or other devices programmable for data processing). A second light source is configured to emit light at 660 nm wavelength and is connected to a second spectrometer which detects a light radiation with 700 to 800 nm wavelength, including Raman scattering, this spectrometer being connected to the same processor.

It should be noted that the apparatus provides the use of any number of light sources capable of emitting light with a different wavelength or a range of wavelengths as compared to the other light sources. Similarly, any number of spectrometers can be used, wherein each individual spectrometer corresponds to an individual light source. The apparatus according to said technical solution can measure and determine whether the examined sample is a diamond or a simulant, whether the diamond is a natural diamond or a synthetic one, whether the examined diamond has been subjected to a treatment in order to improve its color, and can determine its size and grade.

Disadvantages of this apparatus include an insufficiently high accuracy of identification caused by the fact that the apparatus cannot detect the N3 nitrogen center defect most characteristics and commonly found in natural diamonds, which is currently considered a reliable feature of natural origin of diamond; this fact can result in false diagnosis of natural and synthetic diamonds. Other disadvantages are the large overall dimensions of the apparatus due to the use of at least two spectrometers, lack of mobility, and inability of testing cut diamonds (brilliants) in jewelry.

SUMMARY OF THE INVENTION

An object of the present technical solution is to provide a compact mobile apparatus having a built-in independent power supply, which apparatus ensures effective identification of cut diamonds (brilliants), and has a simplified structure due to the use of only a single spectrometer for taking measurements by three techniques for diamond identification: Raman scattering, ultraviolet absorption, and photoluminescence. Furthermore, the ability of moving the optical system providing an adjustment of positions of optical fibres relative to the diamond surface depending on an irradiation mode allows for enhancing the radiation detection sensitivity of the spectrometer.

The object of the present technical solution is attained by a diamond identification apparatus according to the invention for identifying a cut diamond, said apparatus comprising a measurement location with a measuring aperture at which the cut diamond to be examined is fixedly positioned; a movable optical system including a spectrometer, two sources of radiation with wavelengths of 250-280 nm and 350-380 nm, respectively, said two sources of radiation and the spectrometer being connected to the measurement location by optical fibres for inputting radiation into the cut diamond and by an optical fibre for outputting radiation from the cut diamond; and also a source of laser radiation with a wavelength of 532 nm, and a microcontroller, wherein the cut diamond is positioned at the measurement location in such a way that the table of the diamond faces the measuring aperture of the measurement location and the culet of the diamond is directly above the measuring aperture to which the optical fibres for inputting radiation and the optical fibre for outputting radiation are led, and wherein the microcontroller is configured to control alternate operation of the sources of radiation in a set time sequence, movement of the optical system to allow the input of the radiation into the cut diamond, and processing of the spectrometer data.

Furthermore, the optical fibre for outputting radiation comprises two optical fibre segments optically coupled to each other by two collimating lenses.

The optical system can be configured to be movable such that the optical fibres for inputting and outputting radiation from the source of radiation with wavelengths of 250-280 nm come into direct contact with a surface of the cut diamond.

In addition, the optical system can be configured to be movable such that a gap of 1-2 mm size is formed between the optical fibres for inputting and outputting radiation from the source of radiation with wavelengths of 350-380 nm.

Furthermore, the source of laser radiation is configured to direct laser radiation to the surface of the cut diamond through said gap by means of a mirror mounted between the source of laser radiation and the cut diamond.

The optical system according to the invention further comprises a notch filter adapted to be arranged between the two collimating lenses to attenuate the radiation intensity from the sources of radiation, wherein the notch filter is provided with a moving input/output mechanism for removing the filter from a radiation optical path when the optical radiation is output from the source of radiation with wavelengths of 250-280 nm.

Furthermore, the removal of the notch filter from the radiation optical path is performed responsive to a signal from the microcontroller.

The gist of the invention is illustrated by the drawings of FIGS. 1 to 5.

DESCRIPTION OF EMBODIMENTS

Figure 1:
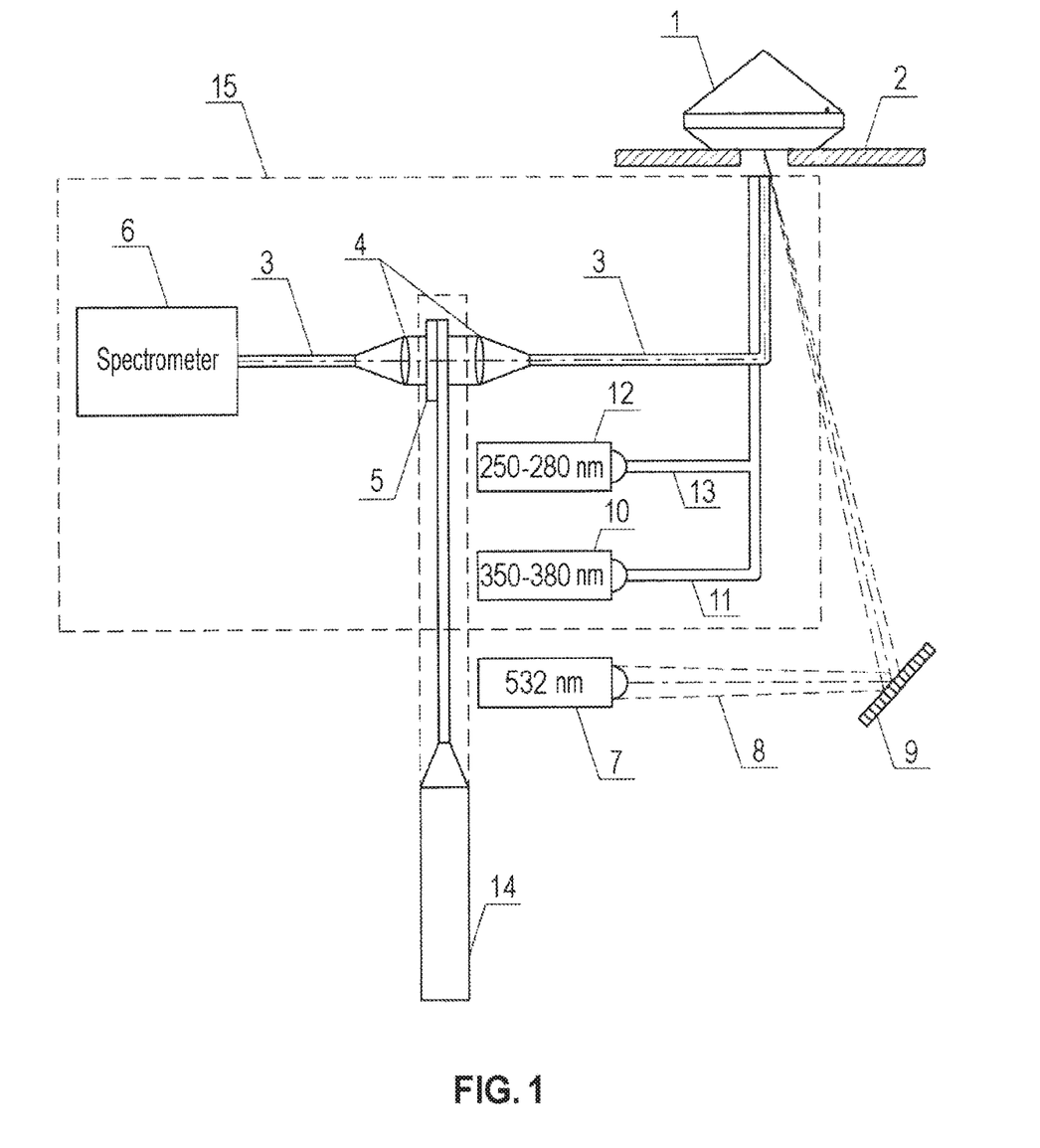
FIG. 1 shows a schematic diagram of the diamond identification apparatus when obtaining spectra of Raman scattering (RSS) and photoluminescence.

FIG. 1 shows a schematic diagram of an apparatus for identifying a diamond 1 mounted at a measurement location 2 with a locking device (not shown) for centering a cut diamond (brilliant) relative to a measuring aperture formed in the center of the measurement location 2 for supplying radiations to a surface of the diamond. Meanwhile, the diamond is mounted at said measurement location 2 such that the diamond covers said aperture. Three optical fibres are used in the apparatus. One optical fibre 3 for outputting radiation is connected to a spectrometer 6 and consists of two segments optically coupled therebetween by two collimating lenses 4 forming parallel beams from the radiations passing through one of the segments of the optical fibre 3. An optical notch filter 5 can be interposed between the collimating lenses 4, which filter is configured to reduce by six orders of magnitude the intensity of a laser radiation with wavelength of 532 nm and by four orders of magnitude the intensity of a broadband radiation of 350-380 nm. Two other optical fibres 11 and 13 for inputting radiation are configured to input into the diamond the broadband radiations of 350-380 nm from a radiation source 10 in the form of a LED to excite photoluminescence, and of 250-280 nm from a radiation source 12 in the form of a LED 13 to measure absorption in the diamond. To excite the Raman scattering, a source of laser radiation (a compact solid-state laser) 7 with a wavelength of 532 nm is used in the apparatus. A focused laser radiation 8 generated by the laser radiation source 7 is directed by a mirror 9 to the sample being examined (cut diamond 1). A notch filter input/output device 14 is shown by a dashed line in FIG. 1. The input/output device represents an electric motor and is controlled by a microcontroller (not shown).

An optical system 15 (shown by a dashed line in FIGS. 1 and 2) includes a spectrometer 6, the radiation sources 10, 12 with the optical fibres (3, 11, 13) for inputting and outputting radiation, and is configured to be movable, e.g. by a moving device in the form of a movable platform (not shown) on which the above-mentioned elements of the diamond identification apparatus are mounted.

Figure 2:
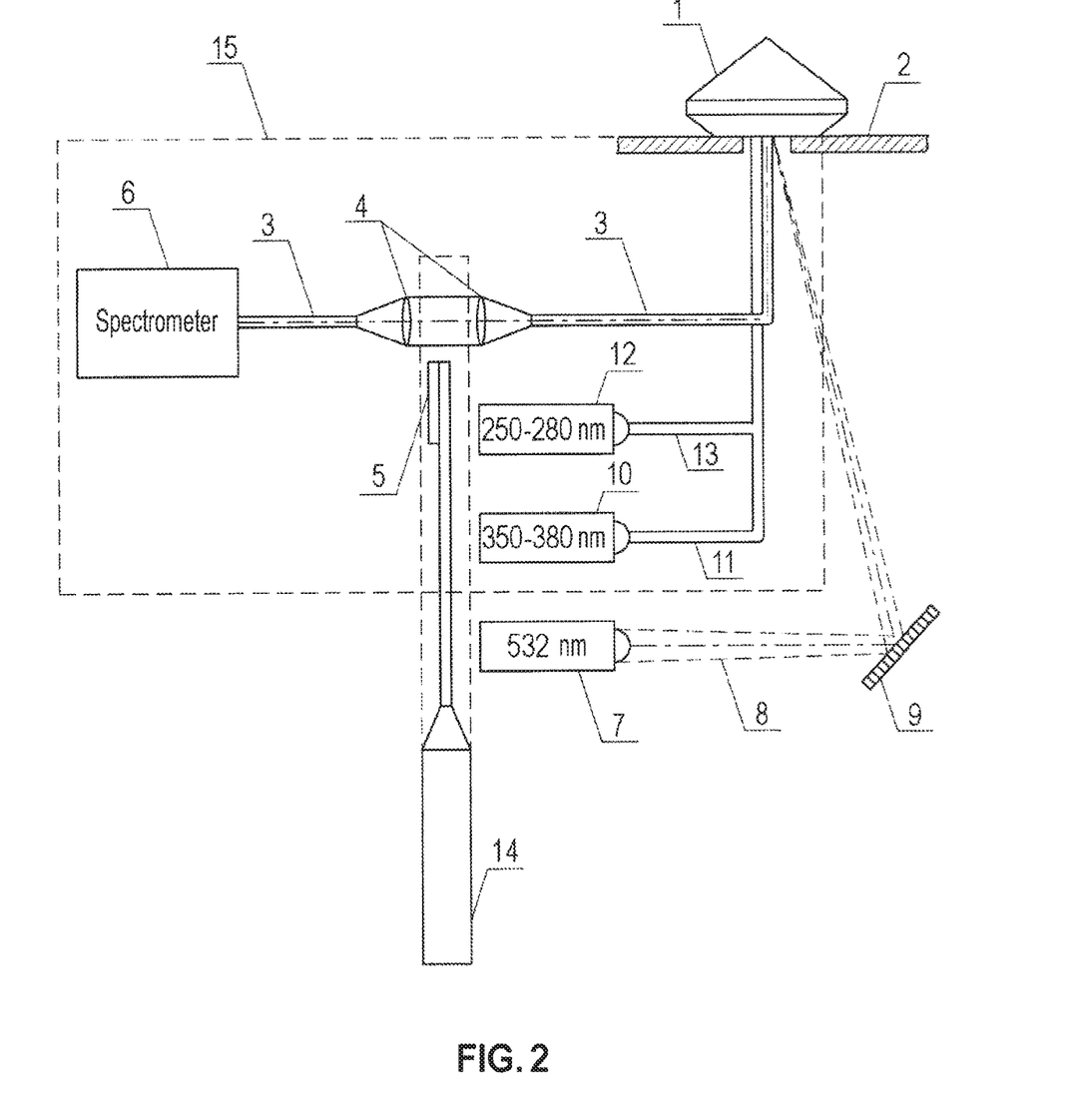
FIG. 2 shows a schematic diagram of the diamond identification apparatus when obtaining transmission spectra in the range of 250-280 nm.

FIG. 2 shows an arrangement embodiment of the diamond identification apparatus when measuring the absorption of short-wave ultraviolet radiation (250-280 nm) in the diamond, which differs from the embodiment of the diamond identification apparatus of FIG. 1 in that the optical fibres 3, 11 and 13 contact the surface of the cut diamond (brilliant), and the notch filter 5 is removed from the optical path of the radiation under analysis. Direct contact of the optical fibres with the diamond makes it possible to detect even weak signals.

The Diamond Identification Apparatus Works in the Following Manner.

In a first examination step, it is verified whether the sample being examined is a diamond, wherein the sample of a cut diamond (brilliant) 1 is positioned onto the measurement location 2 and is fixed with its table towards the measuring aperture such that the culet is directly above the measuring aperture, strictly midway between the optical fibres for inputting and outputting radiation (FIG. 2). Here, responsive to a signal from the microcontroller (not shown), the entire optical system 15 including the radiation sources 10, 12, the three optical fibres for inputting and outputting radiation, the spectrometer 6, the collimating lenses 4 and the notch filter 5 is moved by the moving device so as to form a gap of 1-2 mm between the optical fibres for inputting and outputting radiation and the cut diamond 1 for passing the laser radiation from the laser radiation source 7 initiated by a signal from the microcontroller (FIG. 1). The compact solid-state laser with a wavelength of 532 nm is used as the laser radiation source for obtaining a Raman scattering spectrum. The laser radiation source 7 generates a focused beam 8 responsive to a signal of the microcontroller, which beam is directed using the mirror 9 to the cut diamond (brilliant). Here, the mirror 9 is disposed between the laser radiation source 7 and the diamond 1. The notch filter 5 attached to a supplementary filter input/output moving mechanism 14 is inserted between the collimating lenses 4 disposed between the two optical fibre segments, which filter reduces the intensity of the scattered laser radiation from the sample at the wavelength of 532 nm by the 6 orders of magnitude.

Figure 3:
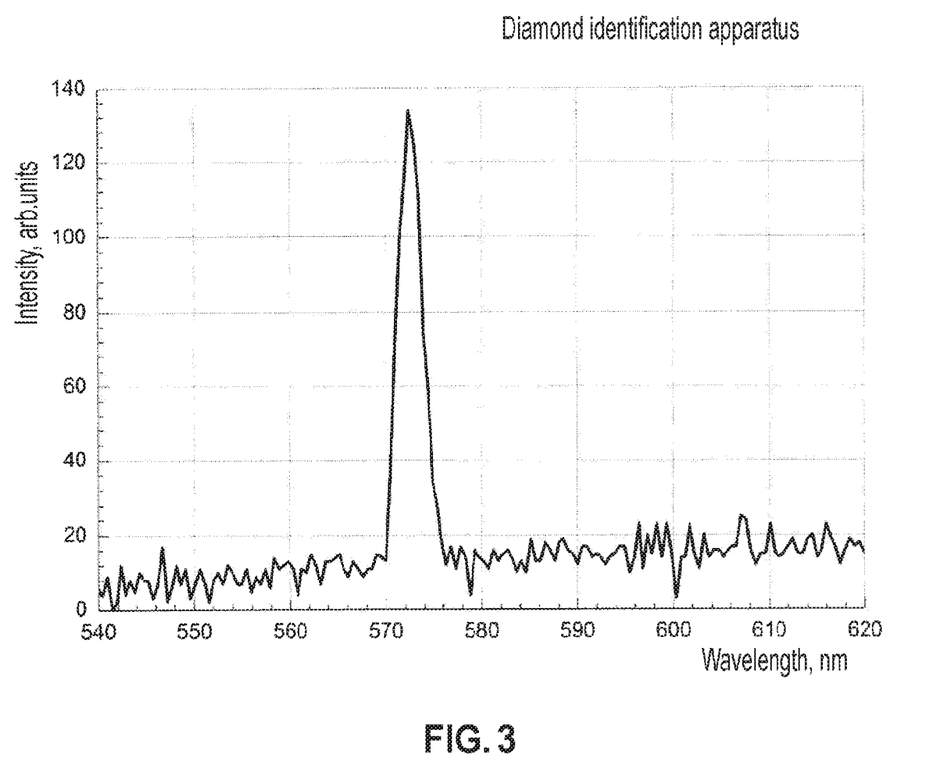
FIG. 3 shows a diamond RSS spectrum with a characteristic line at 1332 $cm^{-1}$.
Figure 4:
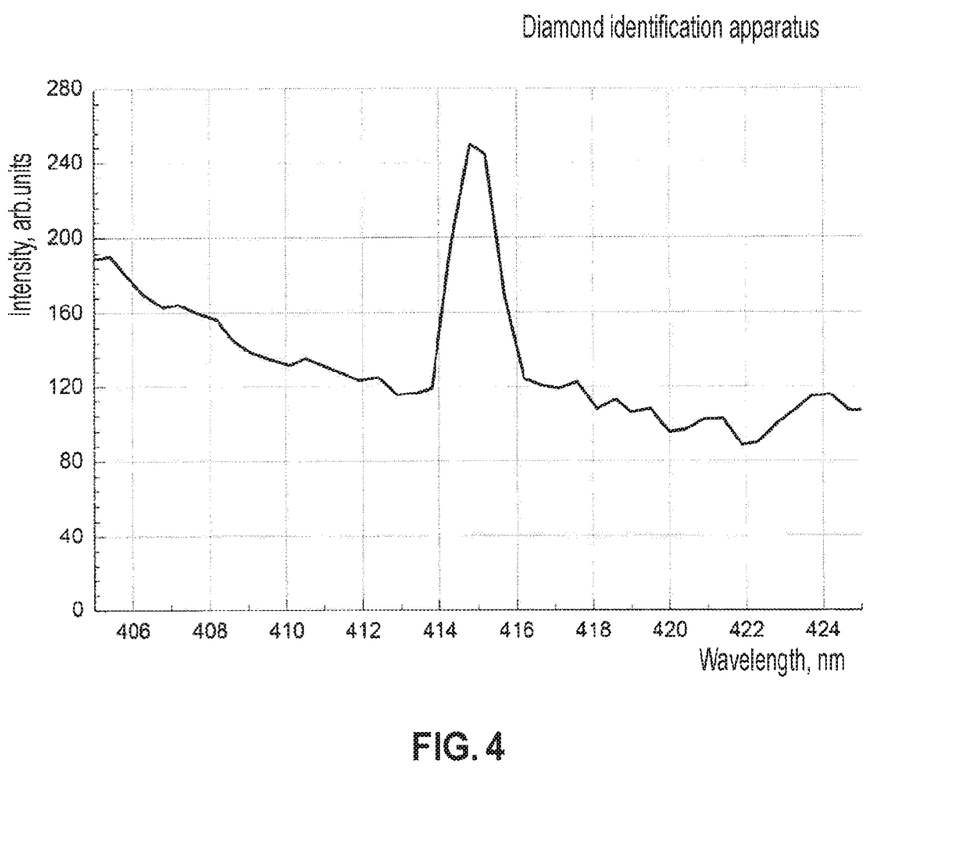
FIG. 4 shows a photoluminescence spectrum of a natural diamond with a 415 nm line.
Figure 5:
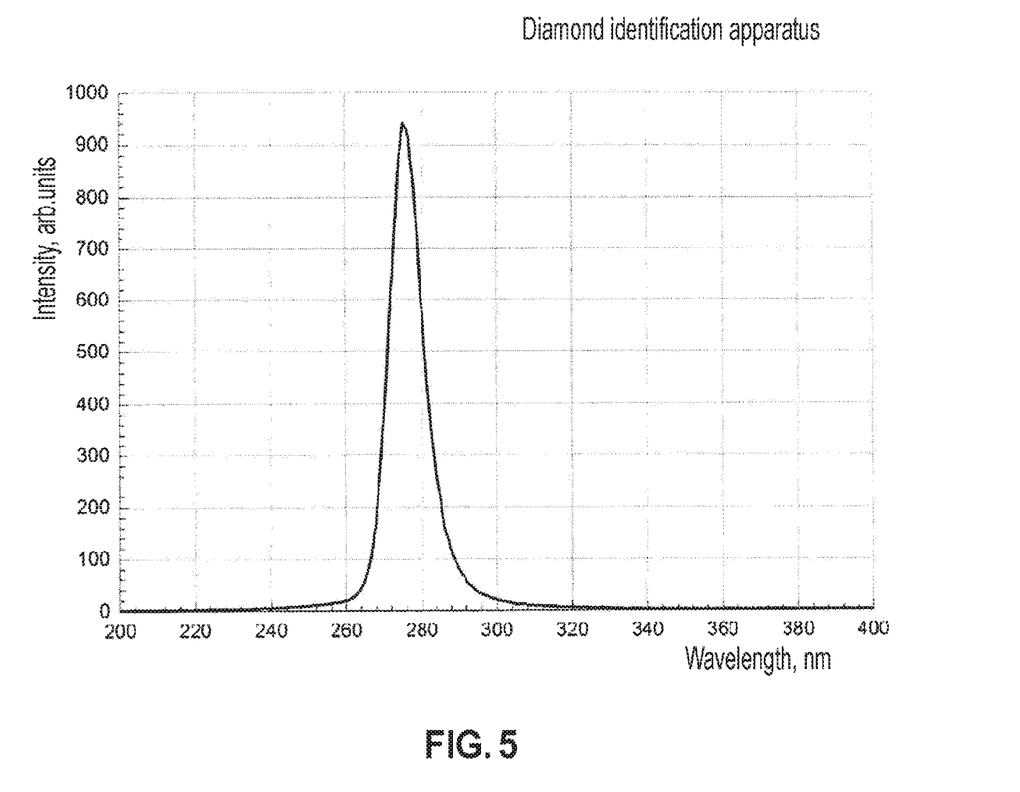
FIG. 5 shows a transmission spectrum typical for Type IIa diamonds.

A resulting spectrum of the sample (diamond) being examined is shown in FIG. 3. The presence of a characteristic diamond line, 1332 cm$^{-1}$ (572.6 nm), indicates that the sample being examined is a diamond.

It should be noted that controlling the radiation sources (turning on/off), the notch filter input/output device, the movement of the optical system, and also a process of processing the spectrometer data are performed by the microcontroller. The spectrometer measurement results are processed in the microcontroller and results of identification of the cut diamonds are output on an electronic display (not shown) connected to the microcontroller.

In a second examination step, it is verified whether the sample being examined is a natural diamond. Here, the second examination step is performed in the same optical circuit shown in FIG. 1, when responsive to a signal from the microcontroller (not shown), the entire optical system 15 including the radiation sources 10, 12, the three optical fibres for inputting and outputting radiation, the spectrometer 6, the collimating lenses 4 and the notch filter 5 is moved by the moving device so as to form a gap of 1-2 mm between the optical fibres for inputting and outputting radiation and the cut diamond 1 for passing the broadband radiation from the radiation source 10 initiated by a signal of the microcontroller (FIG. 1).

In order to determine whether the diamond is natural, a technique for analyzing the diamond luminescence at a wavelength of 415 nm (optically active N3 center) is used. To excite luminescence, the radiation source 10 in the form of a LED having an emission band within the range of 350-380 nm is used to generate a radiation which is directed through the optical fibre 11 to the cut diamond (brilliant) 1. Next, the diamond photoluminescence caused by exposure to the LED radiation is detected via the optical fibre 3 by the spectrometer 6. It should be noted that, when the radiation source 10 operates within the wavelength range of 350-380 nm, a gap is formed between the optical fibre 11 for inputting radiation and the surface of the cut diamond (brilliant). This gap makes it possible to detect, at a constant solid angle, a greater photoluminescence flux by the optical fibre 3 for outputting radiation and, accordingly, to get results at a higher sensitivity. Moreover, the notch filter 5 inserted between the collimating lenses 4 of the optical fibre 3 segments reduces the intensity of scattered radiation from the LED 10 by four orders of magnitude. Note that we use the same notch filter 5 in the two examination steps described above. The presence of the spectral line in the diamond luminescence spectrum at a wavelength of 415 nm (FIG. 4) testifies that the diamond being examined is natural.

In a third examination step, transmission of an ultraviolet radiation of 250-280 nm through the cut diamond (brilliant) is studied. For this purpose, the radiation source 12 in the form of a LED generates the ultraviolet radiation which propagates through the optical fibre 13 onto the cut diamond 1 (brilliant). Having entered the cut diamond through its table, the ultraviolet radiation is successively reflected from opposite pavilion facets of the diamond, goes outside through the same diamond table, and enters the spectrometer 6 through the optical fibre 3.

With this scheme, the ultraviolet radiation passes twice through the crystal body, which makes it possible to get results at a higher sensitivity.

Here, the optical system 15 is moved such that the optical fibres 3, 11, 13 come into close contact with the surface of the cut diamond (brilliant) (FIG. 2). Radiation transmitted by the cut diamond (brilliant) is directed through the optical fibre 3 to the spectrometer 6, wherein the notch filter 5 is removed by the filter input/output mechanism 14. The absence of a band of 250-280 nm in the transmission spectrum of the cut diamond (brilliant) 1 gives evidence of that this is a natural diamond of Type IaA, IaB or IaAB. The presence of a band of 250-280 nm in the transmission spectrum of the cut diamond (brilliant) 1 (FIG. 5) gives evidence of that this is a diamond of Type IIa. If the results of measurements taken by the three techniques show that the examined sample is not a diamond, a "Simulant" legend appears on the electronic display of the diamond identification apparatus. If the examined sample is a natural diamond, then a "Natural Diamond" legend appears on the display. If the examined sample is not a natural diamond, then a "IIa" legend appears. About 2% of natural diamonds, substantially all synthetic (HPHT and CVD) diamonds and natural diamonds that have been subjected to a pressure-and-temperature treatment to improve color can be ascribed to the Type IIa. For reliable identification of these brilliants, they need to be studied in more details.

INDUSTRIAL APPLICABILITY

The inventive apparatus allows for effective identification of diamonds, including in finished jewelry. The applied design solutions make the apparatus compact, mobile and affordable, while ensuring the effective identification of cut diamonds based on the use of the described combination of investigation techniques. The apparatus makes it possible to determine: whether the examined brilliant is a diamond or its simulant, whether this is a natural diamond or a synthetic diamond, and whether more detailed studies are needed to determine whether the examined diamond has been subjected to a pressure-and-temperature treatment.

The invention claimed is:

1. An apparatus for identifying a cut diamond, comprising:
   a measurement location with a measuring aperture at which the cut diamond to be examined is fixedly positioned;
   a movable optical system including a spectrometer, two sources of radiation with wavelengths of 250-280 nm and 350-380 nm, respectively, the two sources of radiation and the spectrometer being connected to the measurement location by optical fibres for inputting radiation into the cut diamond and by an optical fibre for outputting radiation from the cut diamond;
   a source of laser radiation with a wavelength of 532 nm; and
   a microcontroller,
   wherein:
      the cut diamond is positioned at the measurement location in such a way that a table of the cut diamond faces the measuring aperture of the measurement location and a culet of the cut diamond is directly above the measuring aperture to which the optical fibres for inputting radiation and the optical fibre for outputting radiation are led,
      the microcontroller is configured to control alternate operation of the two sources of radiation and of the source of laser radiation in a set time sequence, to control movement of the optical system to allow input of the radiation into the cut diamond, and
      the microcontroller is further configured to control processing spectrometer data.

2. The apparatus according to claim 1, wherein the optical fibre for outputting radiation comprises two optical fibre segments optically coupled to each other by two collimating lenses.

3. The apparatus according to claim 1, wherein the optical system is configured to be movable such that the optical fibres for inputting and outputting radiation from the source of radiation with wavelengths of 250-280 nm come into direct contact with a surface of the cut diamond.

4. The apparatus according to claim 1, wherein the optical system is configured to be movable such that a gap of 1-2 mm size is formed between the optical fibres for inputting and outputting radiation from the source of radiation with wavelengths of 350-380 nm.

5. The apparatus according to claim 4, wherein the source of laser radiation is adapted for directing the laser radiation to a surface of the cut diamond through the gap.

6. The apparatus according to claim 5, further comprising a mirror mounted between the source of laser radiation and the cut diamond, wherein directing of the laser radiation to the surface of the cut diamond is provided by the mirror.

7. The apparatus according to claim 4, further comprising a mirror mounted between the source of laser radiation and the cut diamond, wherein directing of the laser radiation to a surface of the cut diamond is provided by the mirror.

8. The apparatus according to claim 4, wherein the optical system further comprises a notch filter adapted to be arranged between two collimating lenses to attenuate the radiation intensity from the two sources of radiation.

9. The apparatus according to claim 8, wherein the notch filter is provided with a moving input/output mechanism for removing the filter from a radiation optical path when optical radiation is output from the source of radiation with wavelengths of 250-280 nm.

10. The apparatus according to claim 9, wherein the microcontroller is further configured to control the input/output mechanism for removing the notch filter from the radiation optical path.

11. The apparatus according to claim 1, wherein the measuring aperture is formed in a central region of the measurement location for supplying the radiation to a surface of the cut diamond.

* * * * *